(12) United States Patent
Nathe et al.

(10) Patent No.: US 10,849,753 B2
(45) Date of Patent: Dec. 1, 2020

(54) HEART IMPLANT

(71) Applicant: coramaze technologies GmbH, Hilden (DE)

(72) Inventors: Niklas Maximilian Nathe, Düsseldorf (DE); Torsten Scheuermann, Munich (DE)

(73) Assignee: coramaze technologies GmbH, Hilden (DE)

( * ) Notice: Subject to any disclaimer, the term of this patent is extended or adjusted under 35 U.S.C. 154(b) by 121 days.

(21) Appl. No.: 16/080,716

(22) PCT Filed: Feb. 24, 2017

(86) PCT No.: PCT/EP2017/000260
§ 371 (c)(1),
(2) Date: Aug. 29, 2018

(87) PCT Pub. No.: WO2017/148579
PCT Pub. Date: Sep. 8, 2017

(65) Prior Publication Data
US 2019/0021850 A1    Jan. 24, 2019

(30) Foreign Application Priority Data

Feb. 29, 2016 (EP) ..................................... 16000475

(51) Int. Cl.
*A61F 2/24*   (2006.01)

(52) U.S. Cl.
CPC ............ *A61F 2/246* (2013.01); *A61F 2/2463* (2013.01); *A61F 2220/0008* (2013.01)

(58) Field of Classification Search
CPC ................................... A61F 2/24; A61F 2/246
See application file for complete search history.

(56) References Cited

U.S. PATENT DOCUMENTS

2006/0058871 A1   3/2006   Zakay et al.
2007/0255399 A1  11/2007   Eliasen et al.
(Continued)

FOREIGN PATENT DOCUMENTS

CN    101056596    10/2007
EP    2478868      7/2012
(Continued)

OTHER PUBLICATIONS

Notification of Office Action and Search Report dated Sep. 16, 2019 From the State Intellectual Property Office of the People's Republic of China Re. Application No. 201780017361.9. (5 Pages).
(Continued)

*Primary Examiner* — Matthew W Schall

(57) ABSTRACT

The invention relates to a heart implant comprising a tubular attachment element (1) for attaching an inflatable membrane (2), particularly an inflatable membrane (2) being coaxially positioned around the tubular attachment element (1) and fixed to it, the tubular attachment element (1) at one of its ends being split into several strips (4), the strips (4) extending away from the tubular attachment element (1) and forming an expandable cage (C), particularly for fixing the heart implant to the atrium of the heart by surface contact between an exterior surface of the expandable cage (C) and an interior atrium surface, each one of the strips (4) being split into two branches (4a, 4b, 4a', 4b', ... ), each respective branch (4a) being merged into a new strip (5) together with another respective branch (4b') of a neighboring strip (4) wherein such splitting and merging is performed one after the other at least three times and the number of strips (7) being formed of the last merged branches (6a, 6b, ... ) at the end of extension corresponding to the number of strips (4) at the one end of the tubular attachment element (1).

14 Claims, 19 Drawing Sheets

(56) References Cited

U.S. PATENT DOCUMENTS

Figure 1A:
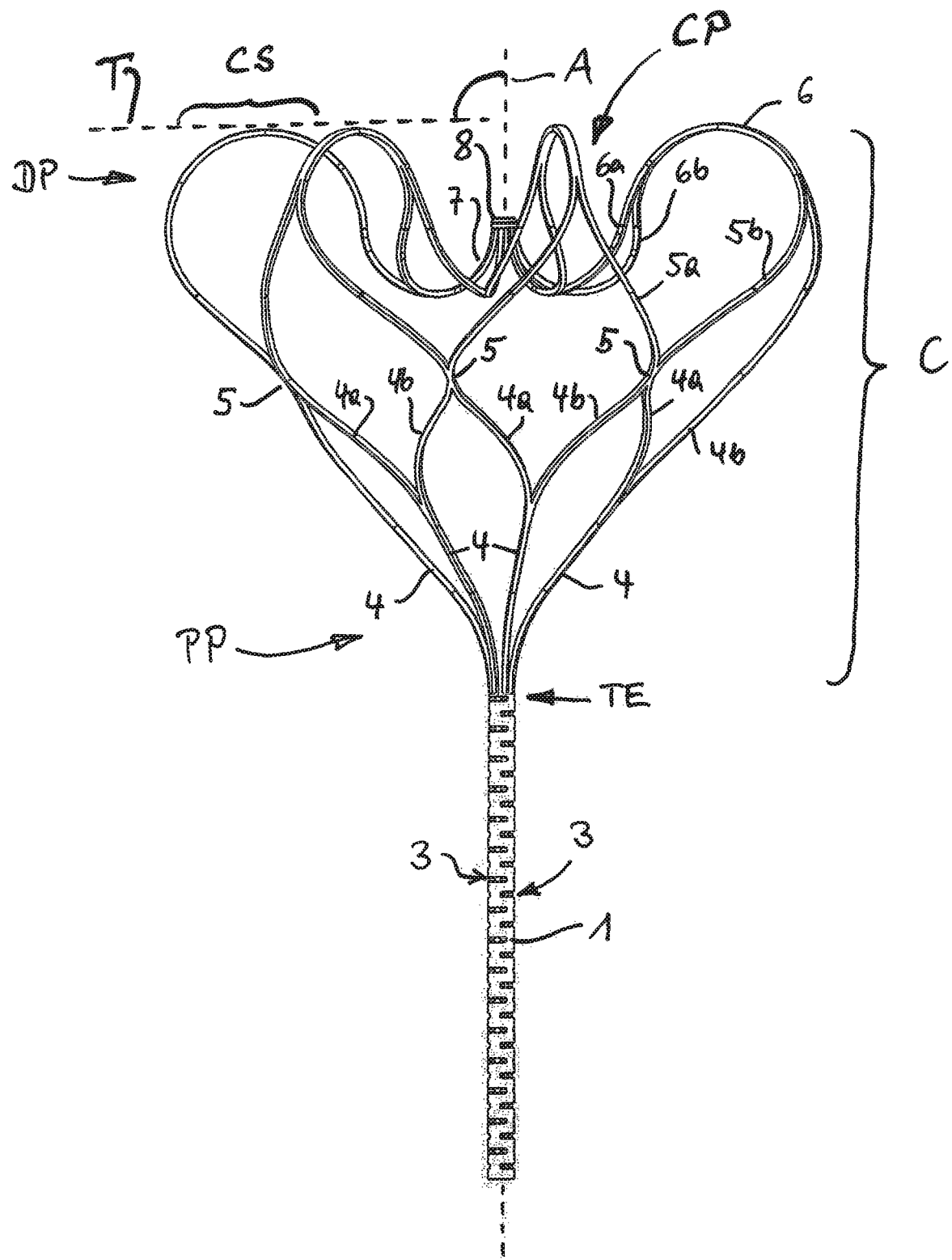

2014/0031928 A1* 1/2014 Murphy ............. A61B 17/0057
623/2.18
2015/0073547 A1 3/2015 Eliasen et al.

FOREIGN PATENT DOCUMENTS

| WO | WO 2012/101190 | 8/2012 |
| WO | WO 2016/180530 | 11/2016 |
| WO | WO 2017/148579 | 11/2016 |

OTHER PUBLICATIONS

Translation dated Sep. 26, 2019 of Notification of Office Action dated Sep. 16, 2019 From the State Intellectual Property Office of the People's Republic of China Re. Application No. 201780017361.9. (2 Pages).

European Search Report and the European Search Opinion dated Aug. 18, 2016 From the European Patent Office Re. Application No. 16000475.0. (6 Pages).

International Preliminary Report on Patentability dated Sep. 13, 2018 From the International Bureau of WIPO Re. Application No. PCT/EP2017/000260. (9 Pages).

International Search Report and the Written Opinion dated Jun. 13, 2017 From the International Searching Authority Re. Application No. PCT/EP2017/000260. (11 Pages).

Communication Pursuant to Article 94(3) EPC dated Jun. 3, 2020 From the European Patent Office Re. Application No. 16000475.0. (6 Pages).

* cited by examiner

HEART IMPLANT

RELATED APPLICATIONS

This application is a National Phase of PCT Patent Application No. PCT/EP2017/000260 having International filing date of Feb. 24, 2017, which claims the benefit of priority of European Patent Application No. 16000475.0 filed on Feb. 29, 2016. The contents of the above applications are all incorporated by reference as if fully set forth herein in their entirety.

TECHNICAL FIELD

The invention relates to a heart implant, particularly a heart implant being configured to reduce or eliminate a heart valve insufficiency after implantation into the heart.

BACKGROUND OF THE INVENTION

Typically such implants are positioned in such a way that a closure element of the implant is situated in the valve annulus and closes a remaining gap of the closed valve leaflets. For that purpose the closure element is connected to an anchoring element being configured to fix the closure element within the heart in the desired position i.e., in the valve annulus preferably to be contacted by the closing valve leaflets.

It is known in the art to use an anchoring element punctured into the myocardium for fixation of the closure element. Besides this invasive way modern implants provide a less invasive fixation just by contacting the interior wall of the atrium with the outer surface areas of an expanded cage that is connected to the closure element. Such cage typically is in a collapsed state for feeding the entire implant through a catheter into the heart where it is expanded after release from the catheter for fixation purposes. The invention relates to such implants having an expandable, preferably mesh-like cage formed of strips for anchoring purposes.

Applicants own patent application DE 10 2015 005 934, which is prior filed and post published already discloses a heart implant comprising a tubular attachment element for attaching an inflatable membrane to it. After attaching, particular fluid tight attaching such membrane that may be inflated by a liquid the expanded membrane and the tubular attachment element surrounded, preferably coaxially surrounded by the membrane form the aforementioned closure element that is to be positioned in the respective heart valve annulus. The membrane may be made of a flexible or elastic material, preferably a foil. An expanded membrane encircles a space surrounding the tubular attachment element that reduces or eliminates a gap between the leaflets.

It is known from this document that the tubular attachment element at one of its ends is split into several strips extending away from the attachment element and forming an expandable cage along their extension.

In view of the fact that the tubular attachment element and the strips may originate from one single tube by cutting the tubular wall several times in an axial direction the mentioned strips all start their extension from an annular end area of the attachment element and preferably are equally spaced along the circumference of this end.

Each one of the strips is split into two branches and each respective branch is merged into a new strip together with another respective branch of a neighboring strip, thus forming a half mesh between the points of splitting and merging.

A cage having meshes is formed that way for fixing the heart implant to the atrium of the heart by surface contact between the exterior cage surface and the interior atrium surface.

The implant according to the mentioned document is intended to be implanted by exerting a pulling force from the distal end of the implant facing the implantation site when it is positioned in a catheter using a pushing catheter extending through the implant. In view of that such implant cannot be implanted by means of usual pushing techniques due to insufficient flexibility.

The invention relates to an implant having the aforementioned features as described in regard to DE 10 2015 005 934.

It is therefore an object of the invention to provide a heart implant for mammalian patients, preferably humans, suitable to be implanted by pushing the entire device though a catheter. Furthermore it is an object of the invention to provide an implant having sufficient flexibility to follow the curved internal pathway of a catheter if pushed from the proximal side, i.e. the side of the implant facing away from the implantation site when the implant is positioned in the catheter. It is also an object of the invention to provide a method of treatment for preventing or at least reducing blood regurgitation in a diseased heart.

Even though the application of the implant and method is preferred in regard to humans the implant and method of treatment may be also applied to animals, particularly mammalian animals.

SUMMARY OF THE INVENTION

The object is solved by an implant wherein such splitting and merging is performed one after the other at least three times. Particularly such splitting and merging results in a number of strips being formed of the last merged branches at the end of extension corresponding to the number of strips at the said one end of the tubular attachment element.

In view of the fact that by splitting a strip into two branches, preferably by laser cutting the strip in the axial direction, the cross section of each branch is smaller than the cross section of the strip (measured perpendicular to the extension), preferably half the cross section or less than half the cross section of the strip and accordingly the flexibility of the thinner branches is higher than the flexibility of the thicker strips.

Preferably the flexibility of the thinner branches may be at least a factor 2 higher than the flexibility of the strips. Such flexibility may be understood as being complimentary to stiffness (preferably meaning that flexibility is proportional to 1/stiffness), which is the extent to which branches and strips resist deformation in response to an applied force. Applying the same force to branches and strips will in this case result in a higher deformation in the branches compared to the deformation in the strips. Consequently the invention provides that the overall flexibility of the entire cage is improved by providing at least three times the mentioned splitting and merging.

Splitting a strip into branches and merging the side-by-side lying branches of neighboring strips may be achieved by cutting slits into the wall of a tube, the slits being spaced in axial direction and axially offset (interdigitated) in circumferential direction.

In this context it is preferred to provide that along the extension from the one end of the tubular attachment element towards the strip end at the last merged branches at least in parts of the extension the length of a branch is bigger than the length of a preceding and/or consecutive strip.

It may be provided according to the invention that at least the tubular attachment element and all strips and branches are formed of the same tube by cutting the tube wall. Such tube may be formed of nitinol as an example. It is also possible to form only the strips and branches of a single tube, preferably a metallic tube, like nitinol tube and to attach that to an attachment element being formed of another tube, preferably of another material, particularly PEEK (Polyetheretherketone) or PET (Polyethylenterephthalate). The different tubes may be fused together.

The invention allows a treatment of heart valve insufficiency in which the collapsed implant according to the invention may be introduced into a placed catheter, an end of which being positioned in the heart, preferably through the valve annulus in the atrium of a mammalian patient, preferably a human. The implant will be pushed through the catheter by applying a pushing force to the end of the implant facing away from the implantation site. The implant is propagated through the catheter until it is released from it into the heart, preferably into the atrium, where it is expanded from the collapsed state to an expanded state for fixation purposes.

Expansion of the cage may be performed automatically after release out of the catheter in view of the fact that the implant/cage is heated to body temperature due to blood contact and thus expands into the teached-in shape of the shape memory material of the cage.

Fixation is performed in a way that a membrane that is attached to the tubular attachment element is positioned within the valve annulus preferably such that the closing leaflets get into contact with the exterior surface of the also expanded membrane, Expansion of the membrane may be done by filling the inner volume of the membrane with a fluid after fixation and positioning or also automatically, for example by means of an internal structure expanding the membrane due to the same mentioned memory effect. Accordingly, a blood regurgitation may be reduced by preventing or at least reducing the remaining gap between the leaflets.

The collapsed state of the implant is understood as a configuration of the implant in which it is suitable to propagate it though the inner free diameter of a catheter. Preferably in this collapsed state all strips and branches are positioned within the exterior diameter of the tubular attachment element (regarded in a cross sectional view perpendicular to the central axis of the tubular attachment element). Furthermore preferred a membrane connected to the tubular attachment element is unfilled in this collapsed state of the implant and wound around the tubular attachment element.

The expanded state of the cage of the implant is a state of expansion, preferably at least slightly below maximum possible expansion of the cage, that is determined for fixation purposes. In this expanded state after implantation the cage tends to further expand and thus exerts a force to the inner heart wall, preferably of the atrium. Preferably in the expanded state of the entire implant also the membrane is expanded in this state, preferably by filling a fluid into it or other internal forces.

Any possible states inbetween these mentioned states are understood as intermediate states having no particular relevance.

According to a first possible embodiment the strips at the end of extension are unitarily connected to an annular element. Providing a unitary connection shall preferably mean that the annular element and the strips are formed of the same original tube being cut axially in the mentioned manner to form strips and branches between the tubular attachment element which may be formed of a first part of the original tube and the annular element which may be formed of a second part of the tube. It is also possible to provide a unitary connection by welding, soldering or gluing an annular element to the end strips.

The distal annular element at the end strips may form a sleeve usable as a pulling handle as known from the mentioned document. Consequently the implant according to the invention may be used in combination with the same implantation technique used for the implant of the mentioned document and may also be used for the usual technique of pushing the implant through the catheter due to the improved flexibility.

According to another embodiment the strips at the end of extension form free ends. Preferably this is performed by cutting a tube in axial direction until the tube end is reached, meaning that the respective cuts between which the strip ends are defined are merging into the abutting face of the tube.

In view of the fact that the strip ends are not interconnected by the strip or tube material or in another unitary manner a high flexibility is provided at the distal end of the collapsed cage facing to the implantation site, the flexibility being significantly higher compared to the flexibility of the afore-mentioned embodiment.

In such an embodiment the free ends of the strips may be oriented axially or nearly axially in the collapsed state of the cage formed by the strips and branches. In the expanded state of the cage the abutting faces of the strip ends may face each other or may at least face the central axis of the attachment element. The construction may be also in such a way that an imagined extension of the free ends intersects the central axis or is parallel to the central axis of the attachment element.

Since such an embodiment may have the risk to puncture the myocardium by the free strip ends when releasing the collapsed implant into the atrium the invention may provide further improvements discussed below.

According to a possible improvement in the collapsed state of the cage, preferably being already partly released from the catheter, each one of the free ends may be bent (in a side view in which the end is laterally positioned to the central axis) beyond the central axis of the tubular attachment element. In a side view the end extends from one side of the central axis to the other side by crossing the central axis. In such an embodiment in the (still) collapsed state of the cage the extension of the end strip is transverse to the extension of the central axis and thus also transvers to the direction of movement of the implant at the time of releasing from the catheter into the heart. Even if the catheter opening would face the myocardium the risk is reduced that the end strip will puncture the myocardium.

It is furthermore preferred that in this embodiment also the free ends extend axially, i.e. parallel to the central axis of the tubular attachment element, if the free ends are positioned in the catheter. In this case the entire implant is collapsed. Accordingly the free ends do not have the mentioned bent configuration unless the free ends are released from the catheter and come into contact with blood. This preserves the movability of the implant in the catheter.

Since the free ends are the first part of the implant coming into blood contact after at least partial release from the catheter the free ends will be heated first by the blood contact and gain their aforementioned bent shape prior to the expansion of the remaining part of the cage, preferably meaning that the cage is still collapsed and has not gained any volume even though the free end are already bent.

When further pushing the implant out of the catheter the free ends do not any longer face the myocardium in the direction of the releasing motion and the remaining part of the cage also start to expand due to blood contact and the heating performed by that.

Also in the expanded state of the cage the respective free ends may be bent towards and/or into the inner volume of the cage. This provides that the tips of the free ends are directed away from the myocardium that contact at least some of the strips and for branches of the cage. An improvement may provide that in the expanded state of the cage the free ends of the strips are positioned between the proximal part of the cage and the distal part of the cage. Proximal part of the cage means the part near or closest to the attachment element and distal part means the part of the cage having the biggest distance to the tubular attachment element measured on the central axis of this element.

In a preferred embodiment, which may form a general improvement of all disclosed embodiments, the cage formed of all strips and branches comprises several strips, preferably the respective last but one strips being formed of merged branches that have a curved section being convex to a heart wall and concave towards the proximal part. Such a respective curved section preferably has a tangent perpendicular to the central axis of the tubular element. Accordingly each such curved section comprises a part being bent back from the distal part towards the proximal part of the cage. Each such curved section of a strip may form a first part of an S-shaped configuration wherein the second part of this S-shaped configuration is formed at least in part of branches, particularly the last branches into which the strip is split along the extension.

In another improvement the invention may provide that the respective free ends comprise a pinhole, preferably each one of the free ends. Such pinhole may be used to connect the free ends to each other with a suture filament guided through the pinholes.

Furthermore it is possible to connected the free ends to a connection element, preferably a textile element. A connection may be performed with a suture filament, particularly if the connection element is a textile element. Such connection element, preferably textile element may surround the free ends of the strips at least in the collapsed state of the cage. Such connection element or textile element may form a protective cover and may prevent puncture of the myocardium. A textile element may be formed of an artificial fiber, like PET fibers or PTFE fibers. In general a connection element may be also welded/fused to the free ends. In that case there is no need for pinholes. In this construction the connection element may be formed by a piece of foil.

In a preferred embodiment the connection element/textile element may form an annular element, preferably surrounding the central axis of the attachment element, at least in the expanded state of the cage. The annular surface of the annular element is positioned to cover the tips of the strip ends. In a possible embodiment the free ends are embedded in the annular connection/textile element.

According to another possible improvement each one of the free ends may be covered by a respective sleeve, preferably the sleeve surrounding the tip of the free end and at least partially the free strip end on all sides. Such sleeve may be made of any suitable material, like plastic or even textile material comprising fibers, preferably artificial ones. The sleeves prevent any puncture of the myocardium by the tips of the free ends at the time of releasing the implant from the catheter.

In a preferred embodiment the free ends may be retractable from the sleeves upon pulling the free ends out of the sleeves with a pulling force. It may be provided, that the free ends are retractable only if the pulling force exceeds a set threshold force, that may be defined by the force necessary to overcome a form-closed link or force-closed link between a respective end and a respective sleeve, particularly the link being formed by a projection on the inner surface of the sleeve being positioned in a depression on the outer surface of the end.

In this embodiment it is possible that the myocardium may grow into the sleeves of the free ends, particularly if the sleeves are made of fibers, thus furthermore improving the fixation of the anchoring cage in the atrium. Removal of the implant is also in this case still possible since the cage may be separated from the sleeves fastened to the myocardium by pulling. The separated sleeves may remain in the heart without disturbing the heart function.

No matter whether the free ends are retractable from the sleeves or not the sleeves may be connected to each other. In a first embodiment the respective sleeves may be connected to a star-shaped element, the middle of this element being positioned on the central axis of the tubular attachment element, at least in the expanded state of the cage. In a second embodiment the respective sleeves may be connected to an annular element, the annular element surrounding the central axis of the tubular attachment element, at least in the expanded state of the cage.

In general the expanded cage may be formed from the slotted tube by raising the distance of the cut strips and branches relative to the central axis of the tube at least in an area between the proximal and distal part of the tube. The specific shape of the cage that is intended for fixation purposes in the atrium of the heart may be "teached-in" a shape memory material like nitinol, of which the cage is preferably made.

Another embodiment of the implant may be realized if after at least three times of splitting and merging the last strips formed of merged branches are split again at the end of extension. In that case at the end of extension a number of end branches results that corresponds to twice the number of strips at the aforementioned end of the tubular attachment element where the splitting and the extension of the strips starts. In such case all the features described before in regard to the last (free or connected) end strips may also apply to the last end branches, particularly such last end branches may form free or connected end branches in the same manner as described for the end strips.

DETAILED DESCRIPTION OF THE INVENTION

Preferred embodiments of the invention are described in detail in accordance with the figures.

Figure 1B:
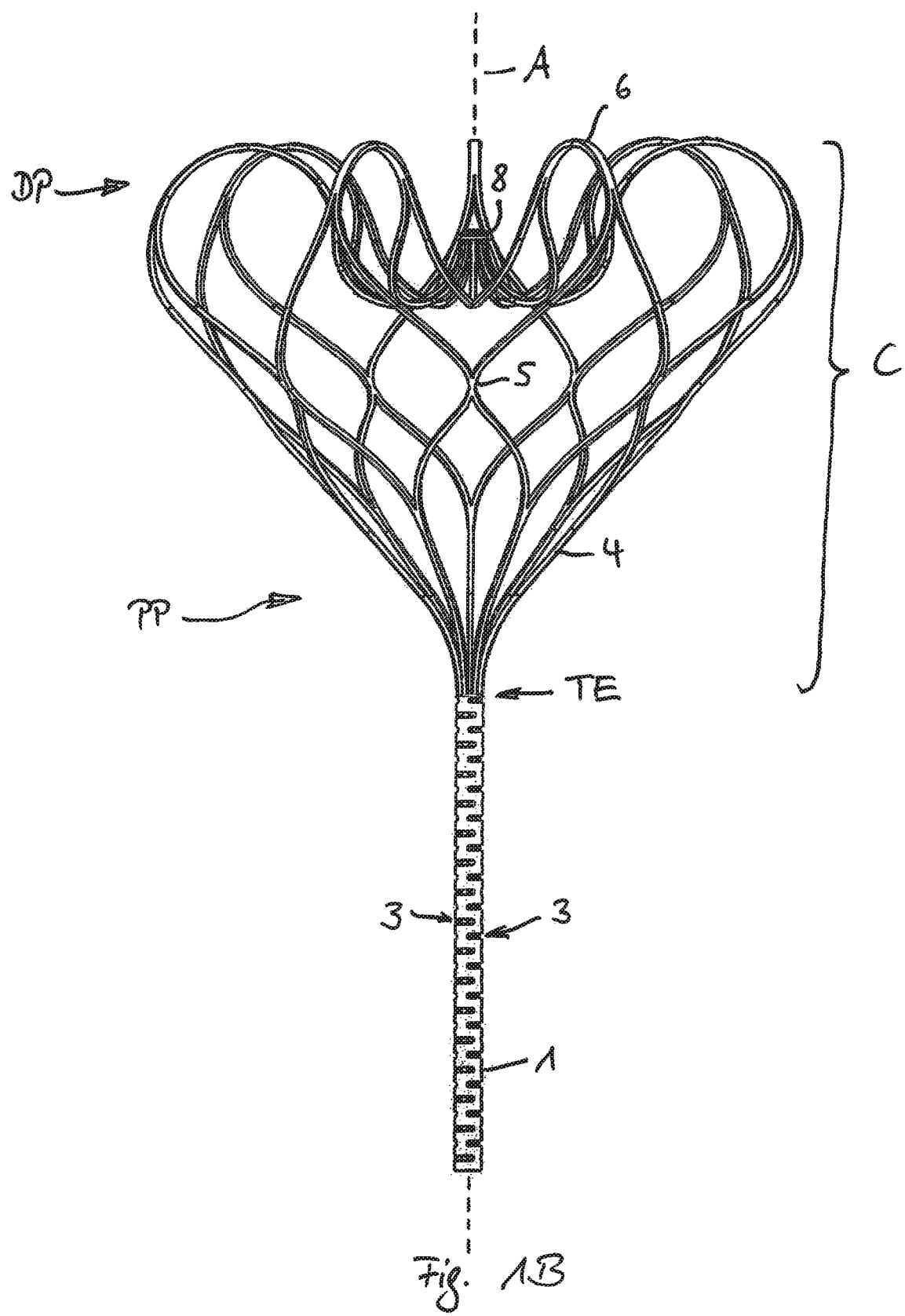
Figure 1C:
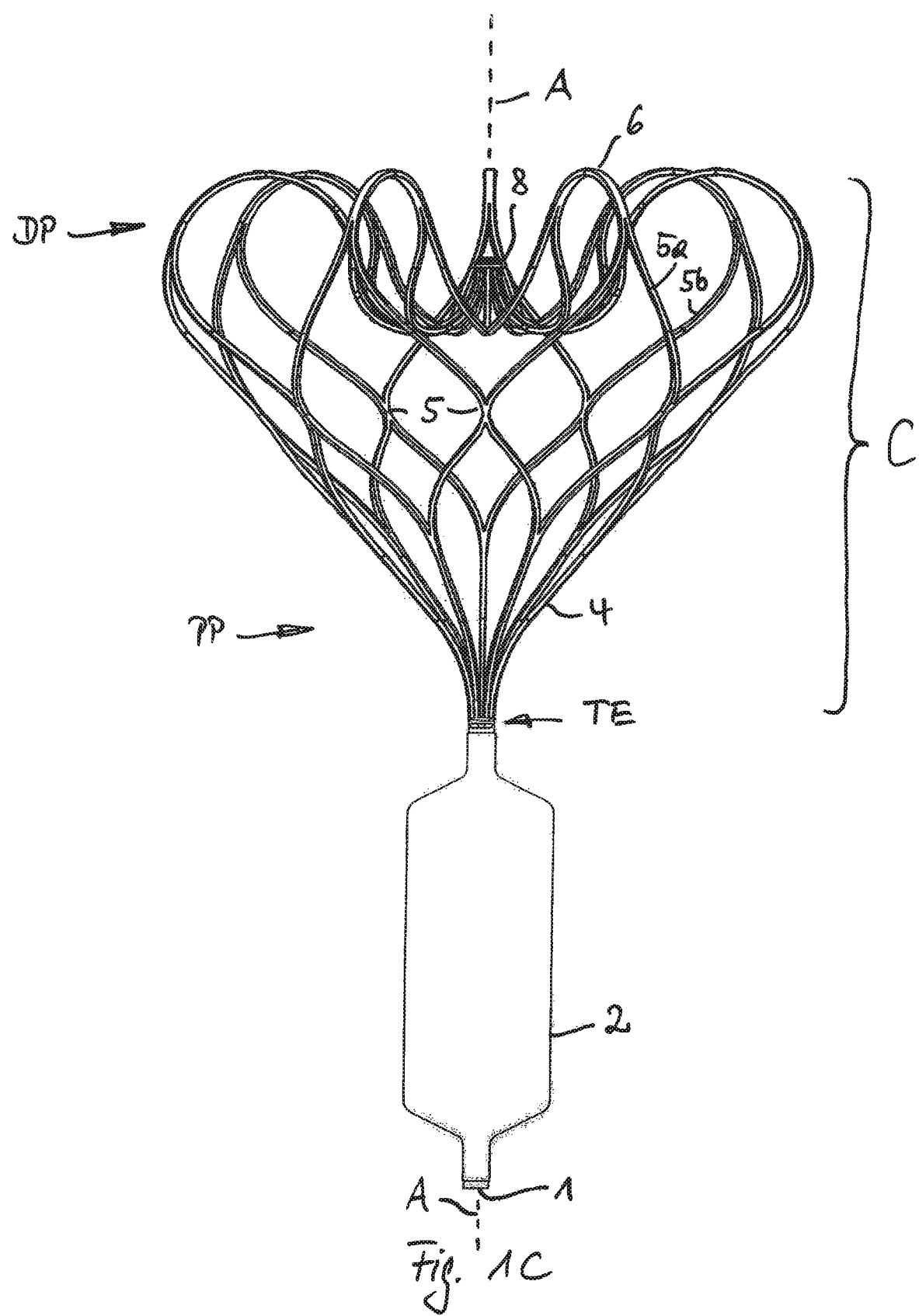

FIG. 1A show a side view of the implant without attached membrane. For better visibility and better explanation only the lines lying in front of the paper plane are shown. Some of the following reference numerals are shown in FIG. 1a only. FIG. 1B shows the same view and all lines. FIG. 1C shows the entire device with a membrane attached to the attachment element. The following description applies for all FIGS. 1A, 1B, 1C.

The lower part of the implant forms an attachment element 1 to which the membrane 2 (shown in FIG. 1C only)

may be attached. Membrane 2 and attachment element 1 form a closure element that may be positioned in the annular area of a heart valve like the mitral valve. Even without the membrane 2 attached the shown device forms an implant according to the invention.

The attachment element 1 is formed of a single tube, preferably made of nitinol. Preferably the necessary flexibility of the tubular attachment element 1 is achieved by providing several cuts 3 in the tubular body of the attachment element 1 in a direction perpendicular to the central axis A. Preferably pairs of opposite cuts 3 are repeated with an axial spacing and interdigitated by an angular offset. This kind of construction may apply to all the embodiments described in the following section and in general.

At the top end TE the attachment element 1 is split into several strips 4, preferably by cutting the same mentioned tube in axial direction. According to the invention each strip 4 is furthermore split into two respective branches 4a and 4b, each branch preferably having a cross section smaller than the cross section of the strip 4. Each one of the branches, for example branch 4a, merges together with another branch, for example branch 4b, of a neighboring strip 4 thus forming a new strip 5 at a distance to strip 4 in the direction of extension from bottom to top. The length of a strip 5 formed by merged branches may be smaller than the length of a preceding branch.

Such splitting and merging is performed for all strips 4 and is consecutively repeated for the strips 5, the following branches 5a, 5b that are merged into strips 6 that are split again into branches 6a, 6b. At last the branches 6a, 6b are merged to a strip end 7. According to the invention splitting and merging is performed at least three times, here exactly three times. This may apply to all the embodiments described in the following section and in general.

The branched areas preferably form the majority in the total extension of the formed cage C thus providing a significant flexibility to the cage, particularly if it is in the collapsed state for feeding the implant through a catheter. Preferably nonetheless the strips formed of connected branches do not only form a singularity of connection but have a lengthwise extension, particularly each strip has an extension of more than 2 mm, preferably between 2 and 15 mm.

In this embodiment the last strips 7 form strip ends that are connected to an annular element 8, formed of the same tube. Here the annular element 8 is positioned between the proximal part of the cage PP and the distal Part DP of the cage C (regarded in the direction of implantation).

The entire cage C may be formed by providing axial cuts in the tubular wall that are axially spaced and interdigitated in circumferential direction. By raising the distance of the so formed strips and branches to the axis A the cage C may be formed. The specific shape of the cage is "teached in" the shape memory metal of the tube, like nitinol.

It can be seen in FIG. 1A that in this preferred embodiment the cage C formed of all strips 4,5,6,7 and branches 4a,4b, 5a, 5b and 6, 6b comprises several strips, preferably the respective last but one strips 6 being formed of merged branches 5a, 5b that have a curved section CS being convex to a non shown heart wall and concave towards the proximal part PP. Such a respective curved section CS preferably has a tangent T perpendicular to the central axis A of the tubular element 1. Accordingly each such curved section CS comprises a part being bent back from the distal part towards the proximal part of the cage. Each such curved section CS of a strip 6 may form a first part of an S-shaped configuration wherein the second part of this S-shaped configuration is formed at least in part of the last branches 6a, 6b into which the strip 6 is spat along the extension. Each one of the last branches 6a, 6b is accordingly bent towards the distal part again and also has a non shown tangent perpendicular to the axis A.

The part of the cage C opposite to the tubular element 1 has a concave part CP surrounding the central axis A and being depressed towards the inner volume of the cage C and preferably concave towards the heart wall. Consequently the connected ends 7 or the free ends 7 of consecutively discussed embodiments will be free of contact to the heart wall. This shown construction may apply to all embodiments of the invention regardless of its illustration in the figures.

Figure 2:
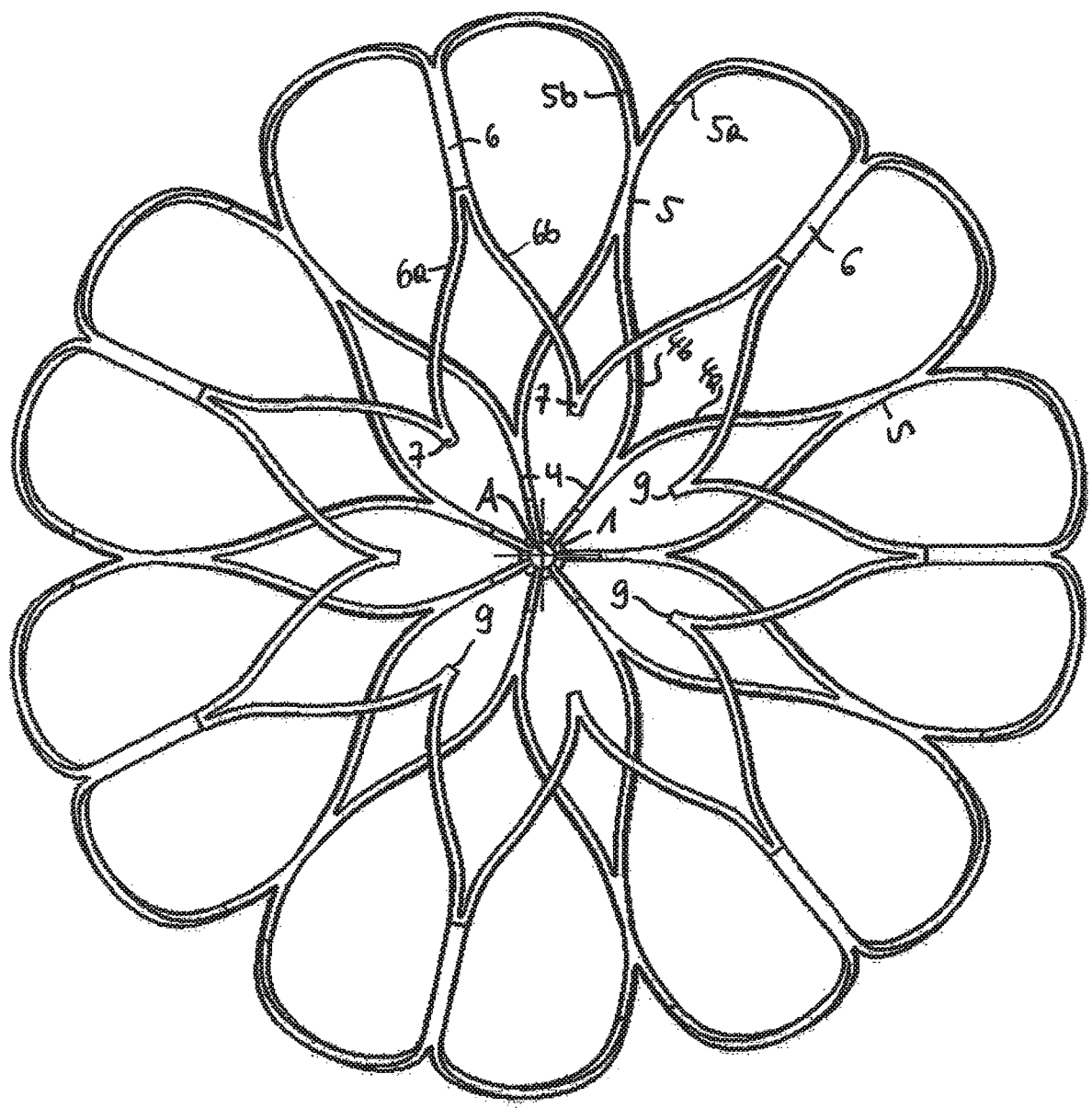

FIG. 2 shows a top view of an embodiment being different to FIG. 1 in the distal part DP of the cage C only. The construction of the strips 4, 5, 6, 7 and branches 4a, 4b, 5a, 5b, 6a, 6b is identical to FIG. 1. In this embodiment the last strips 7, that are formed of the last branches 6a, 6b just form free ends and are not unitarily connected. The tips 9 of the free ends 7 are facing towards the central axis A in the expanded state of the cage as shown.

In the collapsed state the free ends 7 are oriented in the axial direction and form the most distal part of the collapsed cage C. Accordingly there is a risk that the tips 9 may come into contact with the myocardium of the heart at the time of releasing the implant from the catheter and before the cage expands.

Not connecting the strips 7 in a unitary manner and thus forming free ends provide even more flexibility compared to the embodiment of FIG. 1.

Figure 3A:
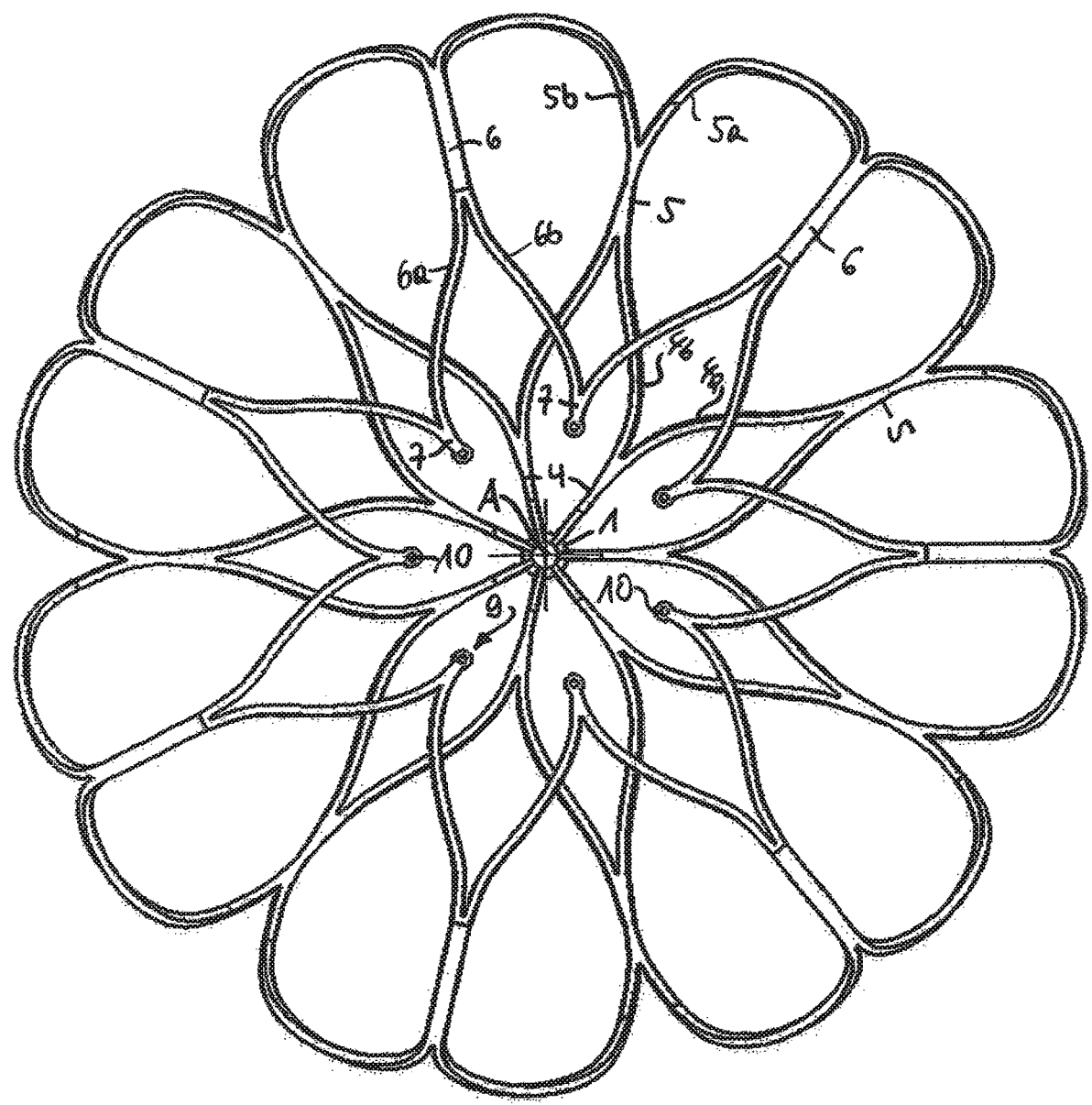
Figure 3B:
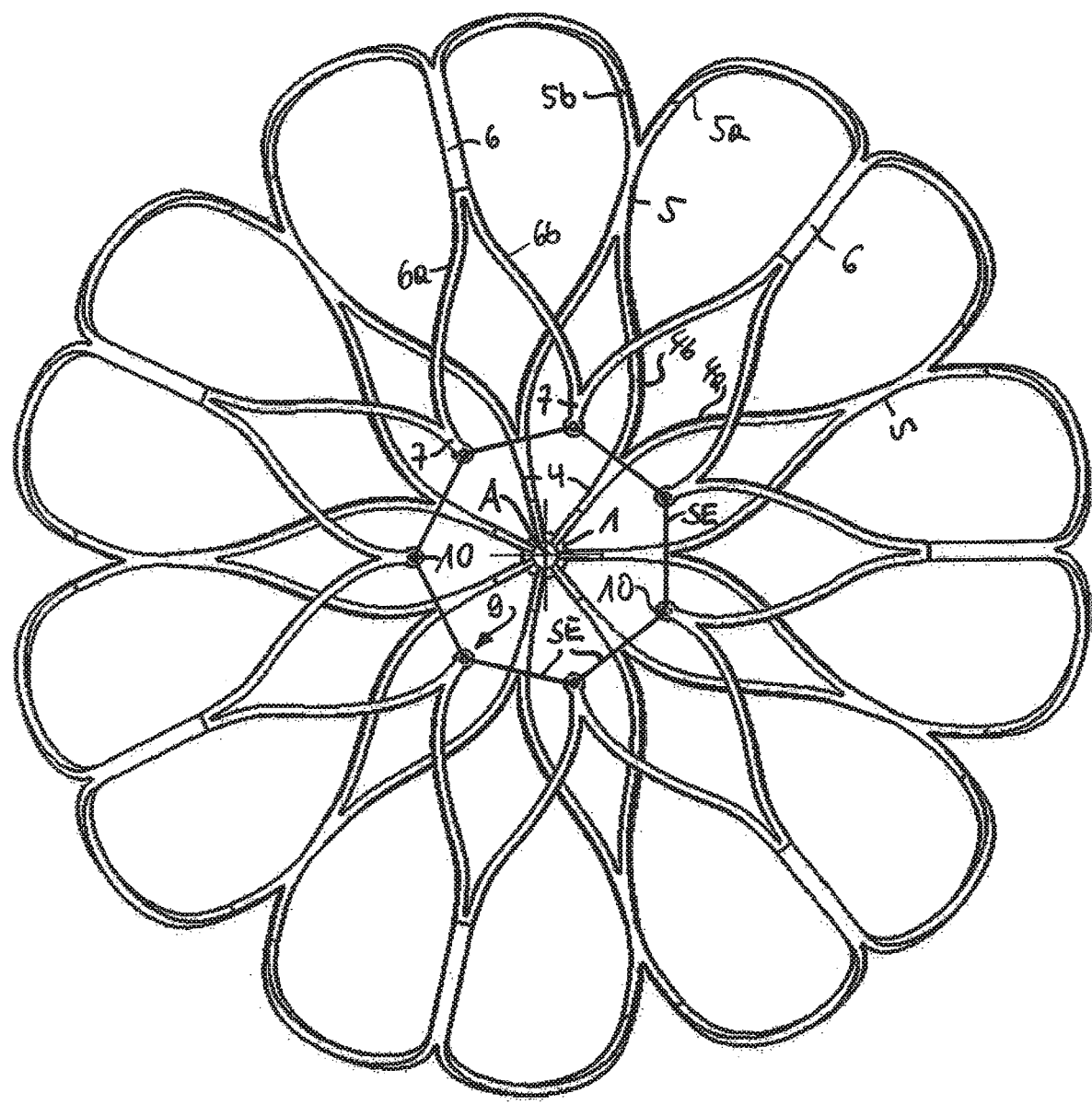

FIGS. 3A and 3B show an improvement of the embodiment in FIG. 2. The construction of the embodiments of FIG. 3A/B are identical to FIGS. 1 and 2 except the tips 9 of the free ends 7 are formed differently. In this embodiment the free ends 7 are each provided with a pinhole 10. The tip 9 has a rounded portion facing the central axis A. Such pinholes 10 may help to connect the free ends 7 to each other by means of an element having a different material, or simply by a suture element SE being guided through the pinholes 10 as shown in FIG. 3B. The connection of the free ends with a suture element SE may provide a stabilized position of the ends relative to each other in the expanded state without affecting the flexibility of the free ends 7.

Figure 4:
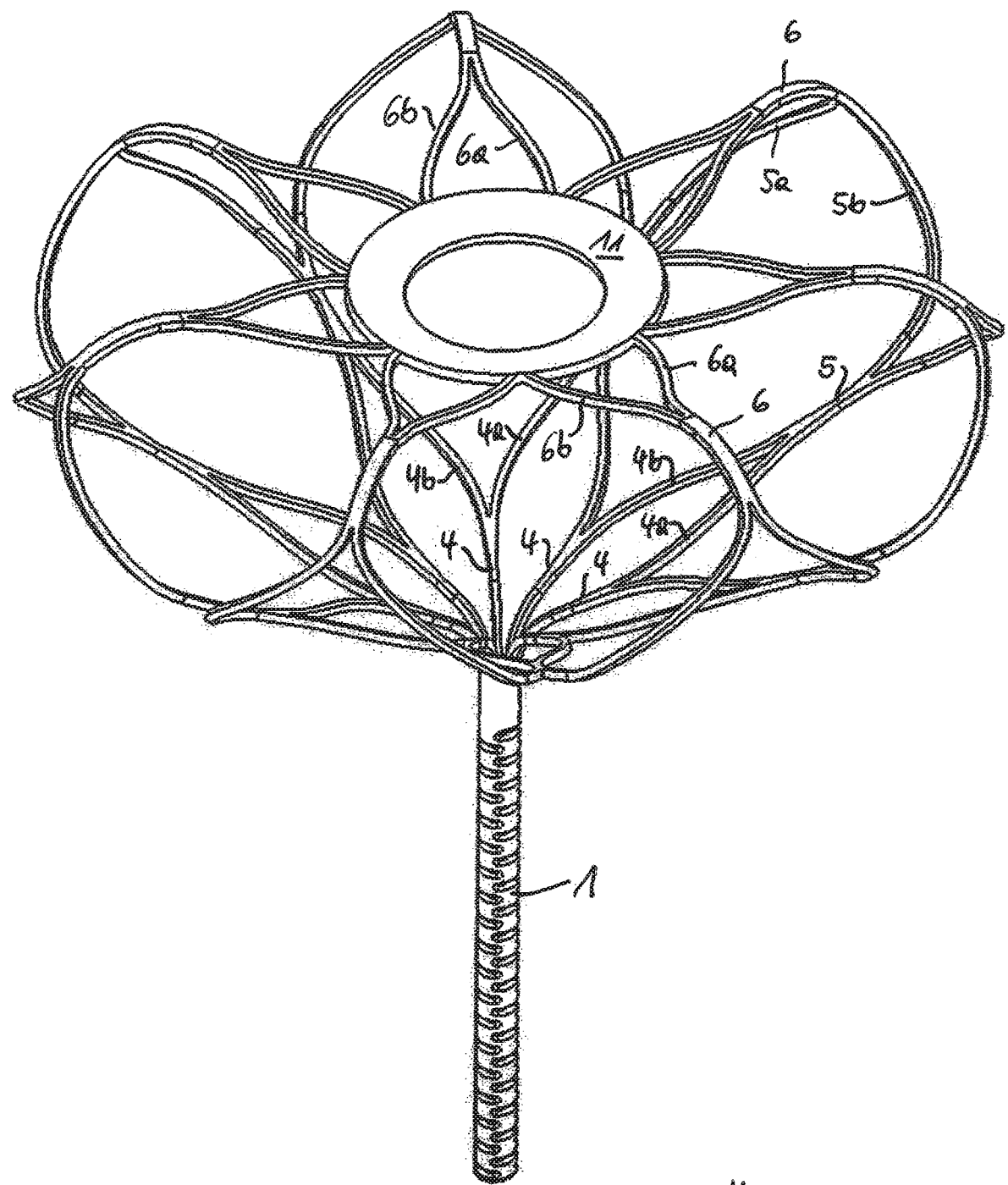

FIG. 4 shows an embodiment in which the free ends 7 are embedded in a annular connection element (11), preferably of a material being different to the free ends 7 that are not shown here due to their encapsulation in the connection element. The annular element 11 may be formed preferably of a textile fabric comprising artificial fibers, like PET- or PTFE-fibers or made of a foil, preferably of the same materials as the mentioned fibers. The element 11 forms a protective cover thus preventing the embedded tips 9 of the free ends 7 to puncture the myocardium at the time of implantation. The connection element 11 may be connected to the free ends 7 for example by means of a suture element, preferably if the free ends 7 have pinholes 10 as shown in FIG. 3. The connection element 11 may also be fused to the free ends 7. The connection element 11 furthermore may cover at least the free strip end 7 and preferably also an end part of the preceding branches 6a, 6b.

FIGS. 5A to 5D show a different kind of protection against the possible risk of puncture by the free ends 7. In this embodiments the free ends 7 of the strips are bent towards/into the inner volume of the cage C, depicted here by just some of the strips/branches.

In the shown expanded state of the cage C the free ends 7 are furthermore positioned between the proximal part PP of the cage and the distal part DP. In addition the free ends (7) and/or the tips 9 of the free ends 7 are facing back to the attachment element 1.

In the corresponding collapsed state the free ends 7 will be oriented transverse or at least not parallel to the central axis A of the attachment element 1. Accordingly the tips 9 cannot harm the myocardium at the time of release from the catheter.

Figure 5A:
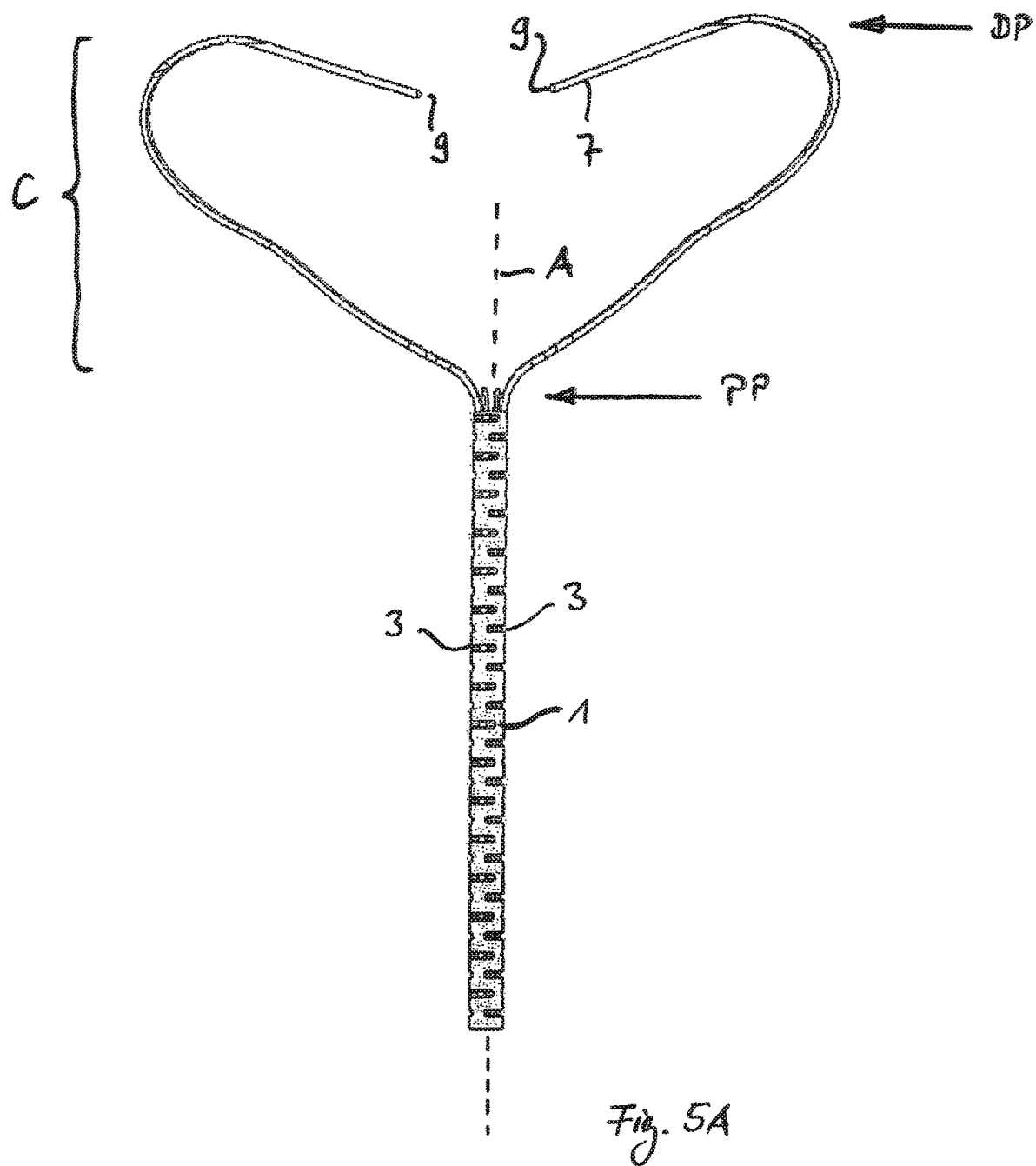

In FIG. 5A the free ends 7 are bent back towards the inner volume of the cage C and towards the tubular element (1). In this case the free ends each have a straight ending, particularly the imagined middle line of such straight ending intersecting the central axis A of the tubular element 1 in the shown cross sectional view, i.e. in a plane parallel to the axis A. Furthermore the tips (9) are facing each other.

Figure 5B:
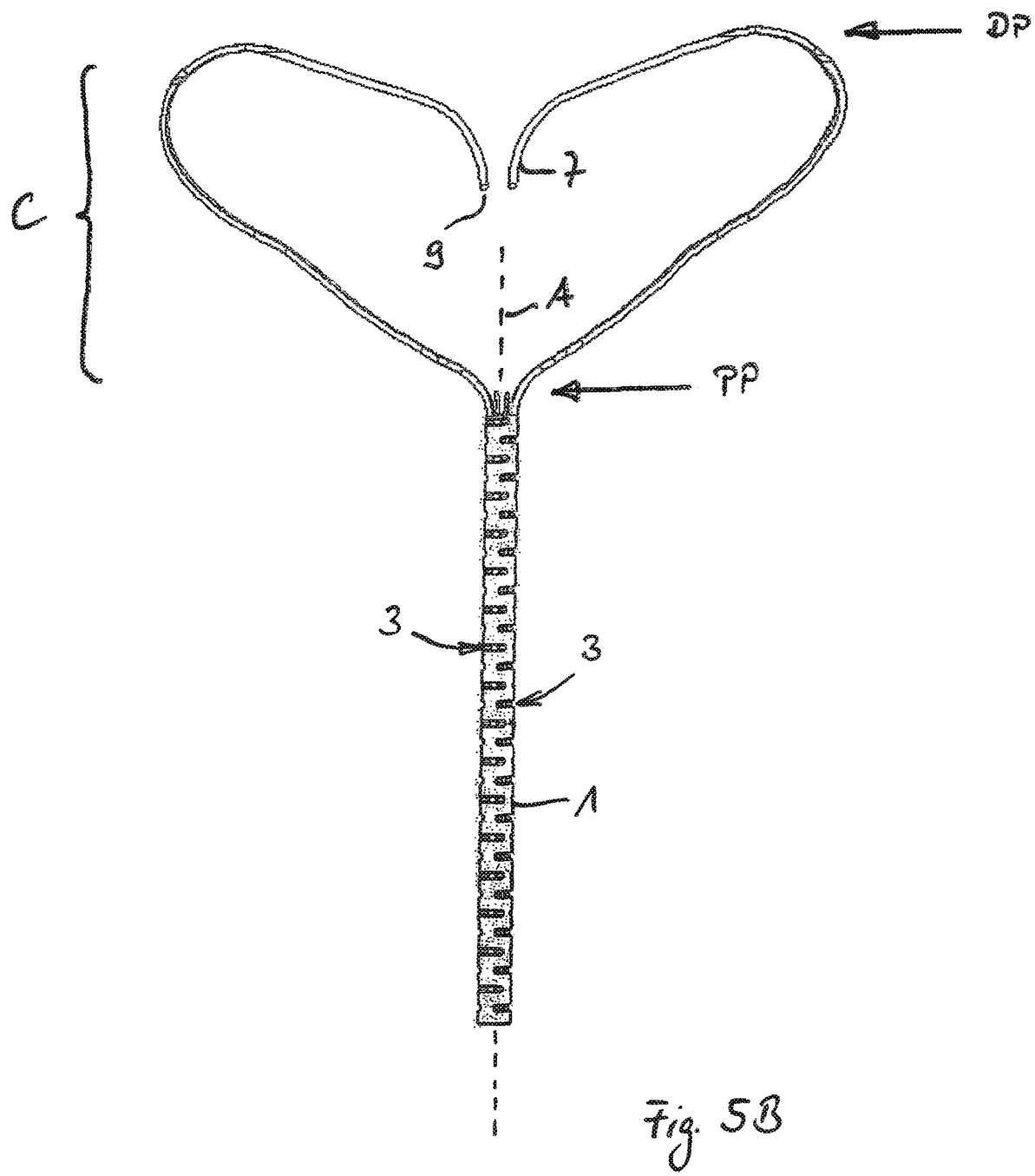

In FIG. 5B the free ends 7 are also bent back towards the inner volume of the cage C and towards the tubular element (1) but here the free ends 7 have a curved ending. The abutting faces of the tips 9 may be perpendicular to the central axis A.

Figure 5C:
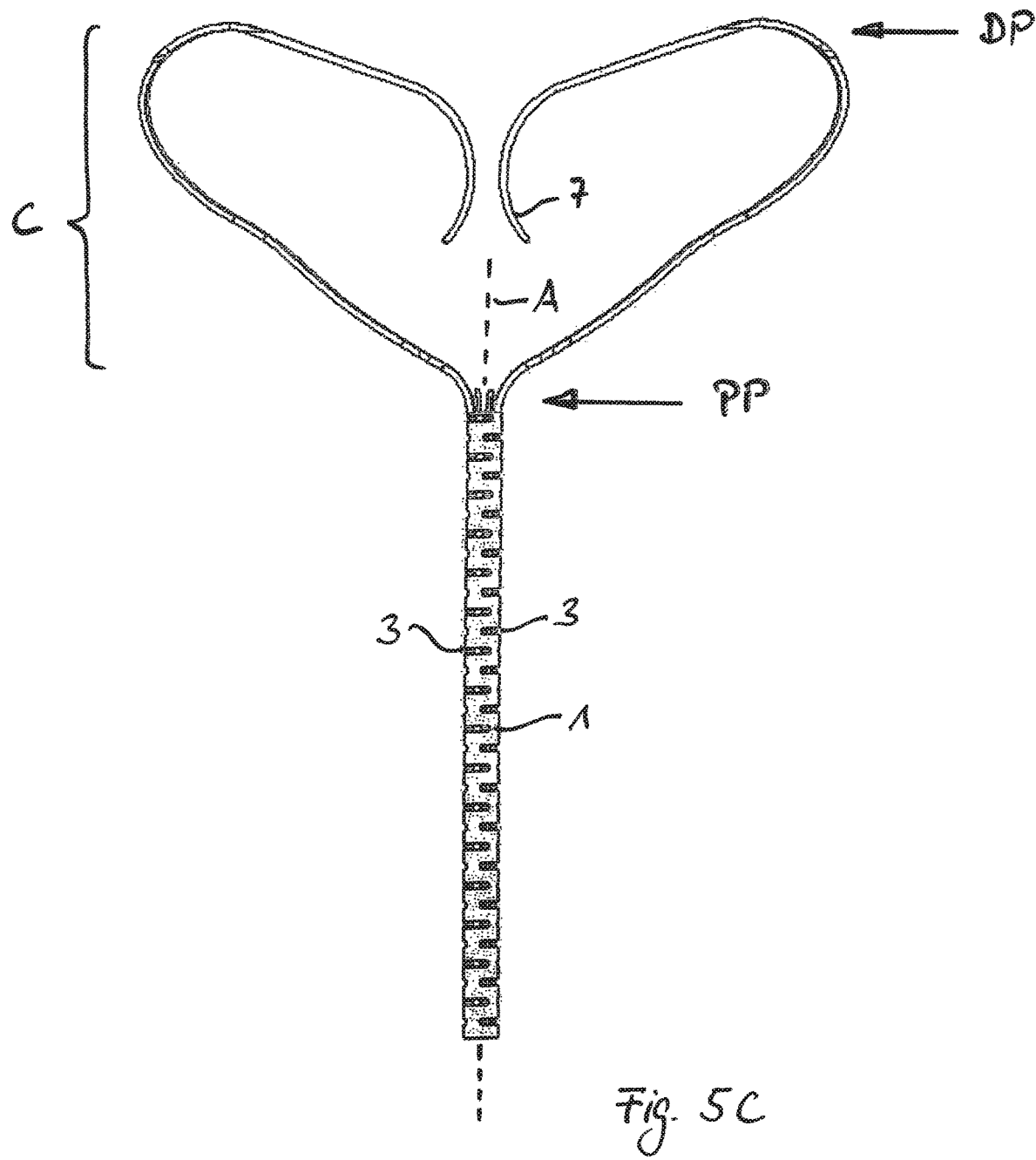

In FIG. 5C the free ends 7 have a curved ending and the tips 9 are facing away from each other, i.e. the normal vectors of the respective abutting faces of the tips 9 are diverging. Furthermore the respective curved parts of the free ends 7 each are convex to the central axis A and to each other.

Figure 5D:
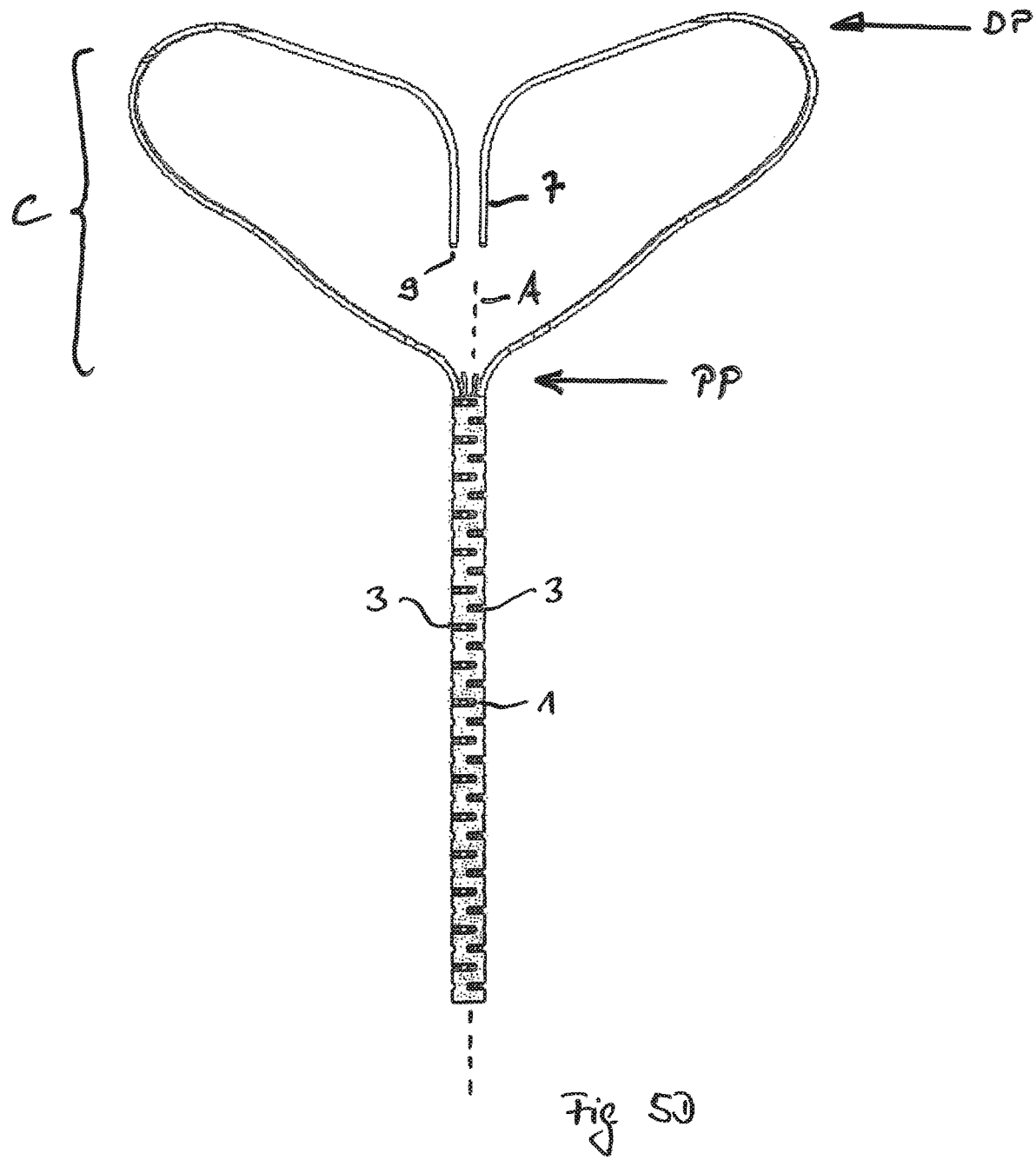

FIG. 5D shows an embodiment in which the free ends are also positioned in the inner volume of the cage C and furthermore form straight endings being parallel to the central axis A of the tubular element 1.

In FIG. 6 a different embodiment is shown in which the free ends of the last strips at the distal part DP are covered in a respective sleeve 12. Each one of the sleeves 12 covers the tip of the free end, the entire last strip 7 and a part of the preceding two branches 6a, 6b.

Figure 6A:
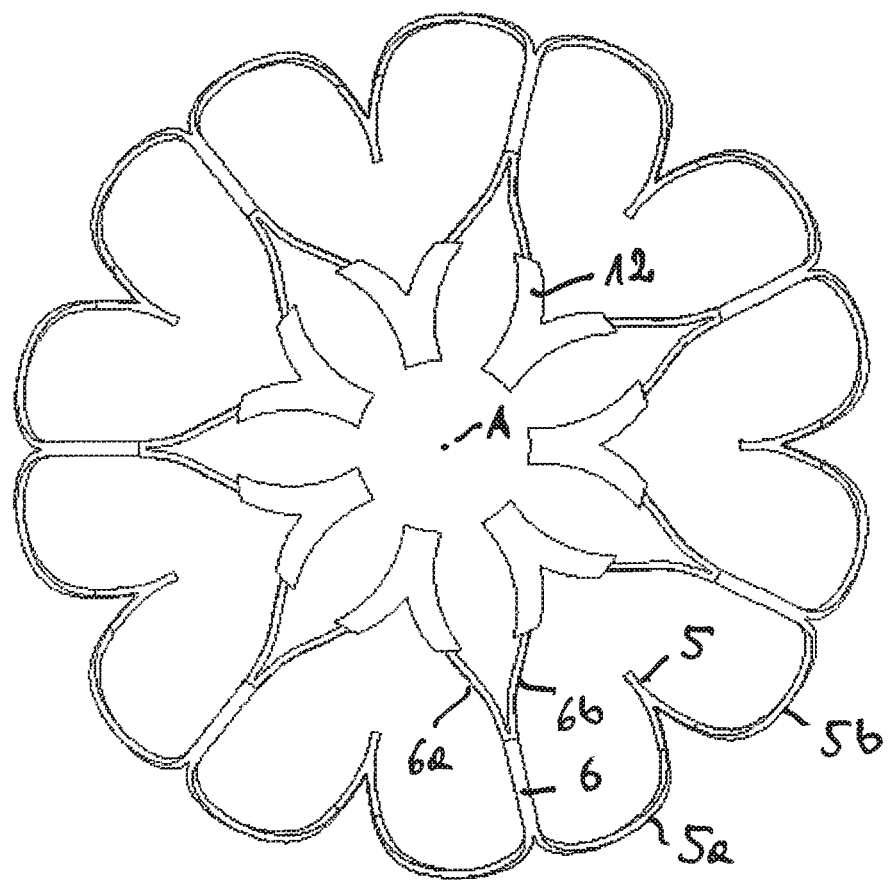
Figure 6B:
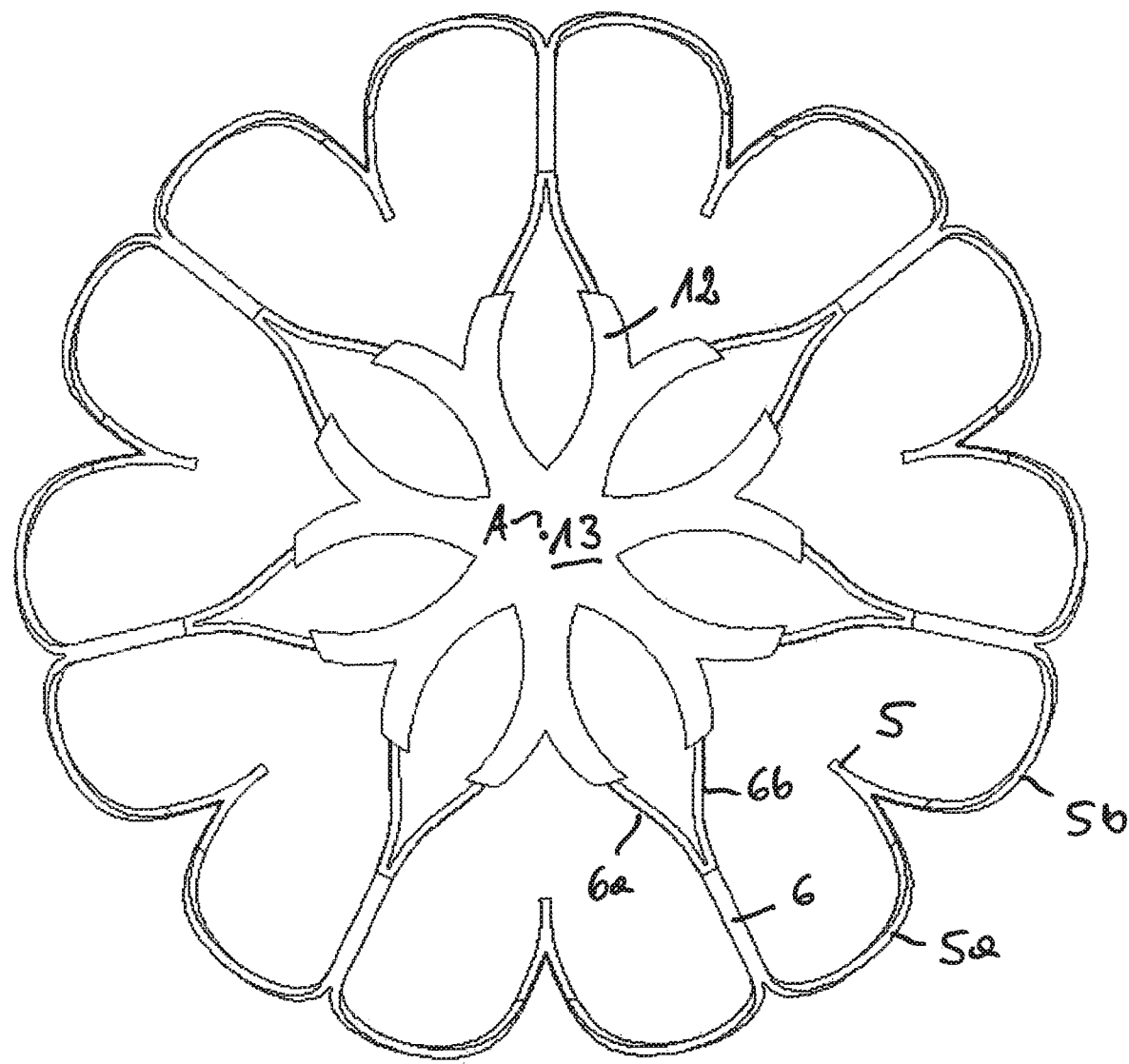

According to FIG. 6a the different sleeves 12 have no connection to each other. According to FIG. 6b the respective sleeves 12 are interconnected by a star-like element 13, the middle of which is positioned on the central axis A in the expanded state as shown.

Figure 6C:
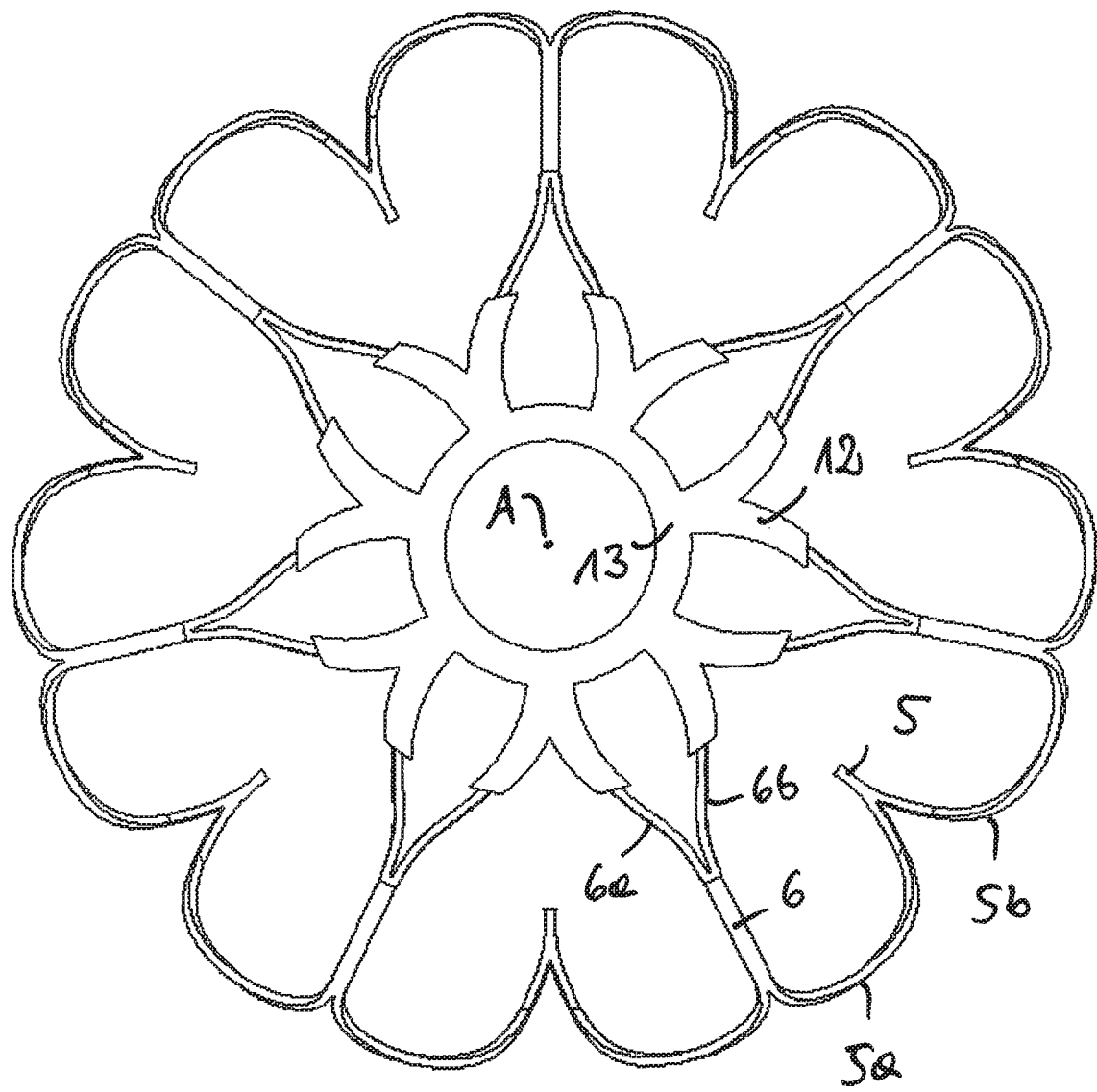

In FIG. 6c the connecting element 13 is an annular element surrounding the axis A.

Figure 7:
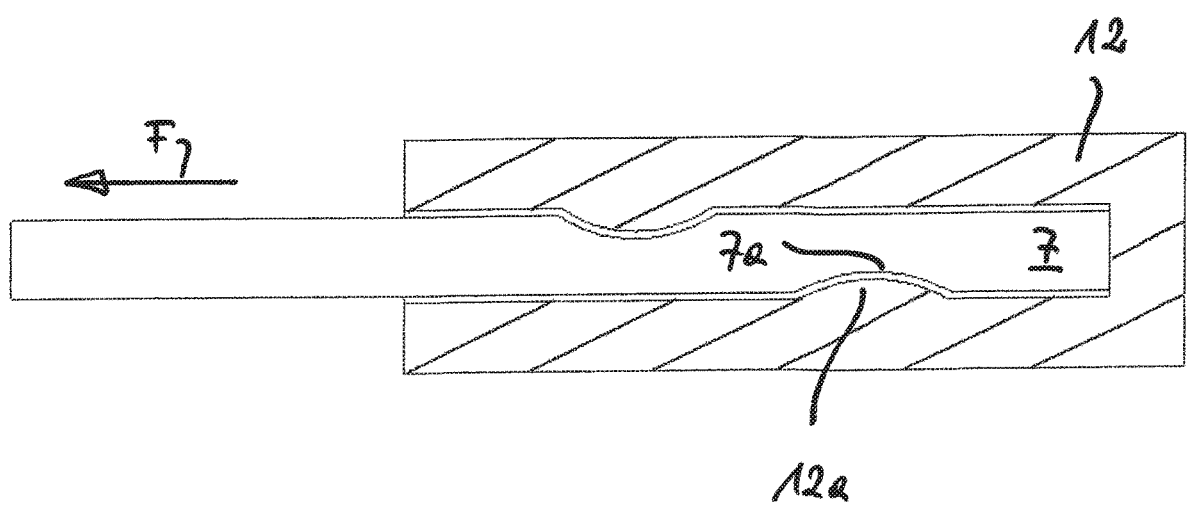

The sleeves 12 in all these embodiment may be formed of a textile or fabric comprising fibers, preferably artificial fibers, like PET, thus providing the advantage that myocardium may grow into the sleeves 12 and the connecting element 13. The sleeves 12 may also be formed of a foil, for example a foil made of PTFE As can be seen in FIG. 7 a form-closed link may be realized between the free ends 7 and the respective sleeve 12. A projection 12a may be positioned in a corresponding depression 7a. The free ends 7 may be retracted from the sleeve 12 for removal of the implant upon exerting a pulling force F to the strip end 7 that overcomes the linking force between the strip 7 and the sleeve 12. In such a case the separated sleeves 12 will remain in the myocardium and the remaining implant is removed from the heart.

Figure 8A:
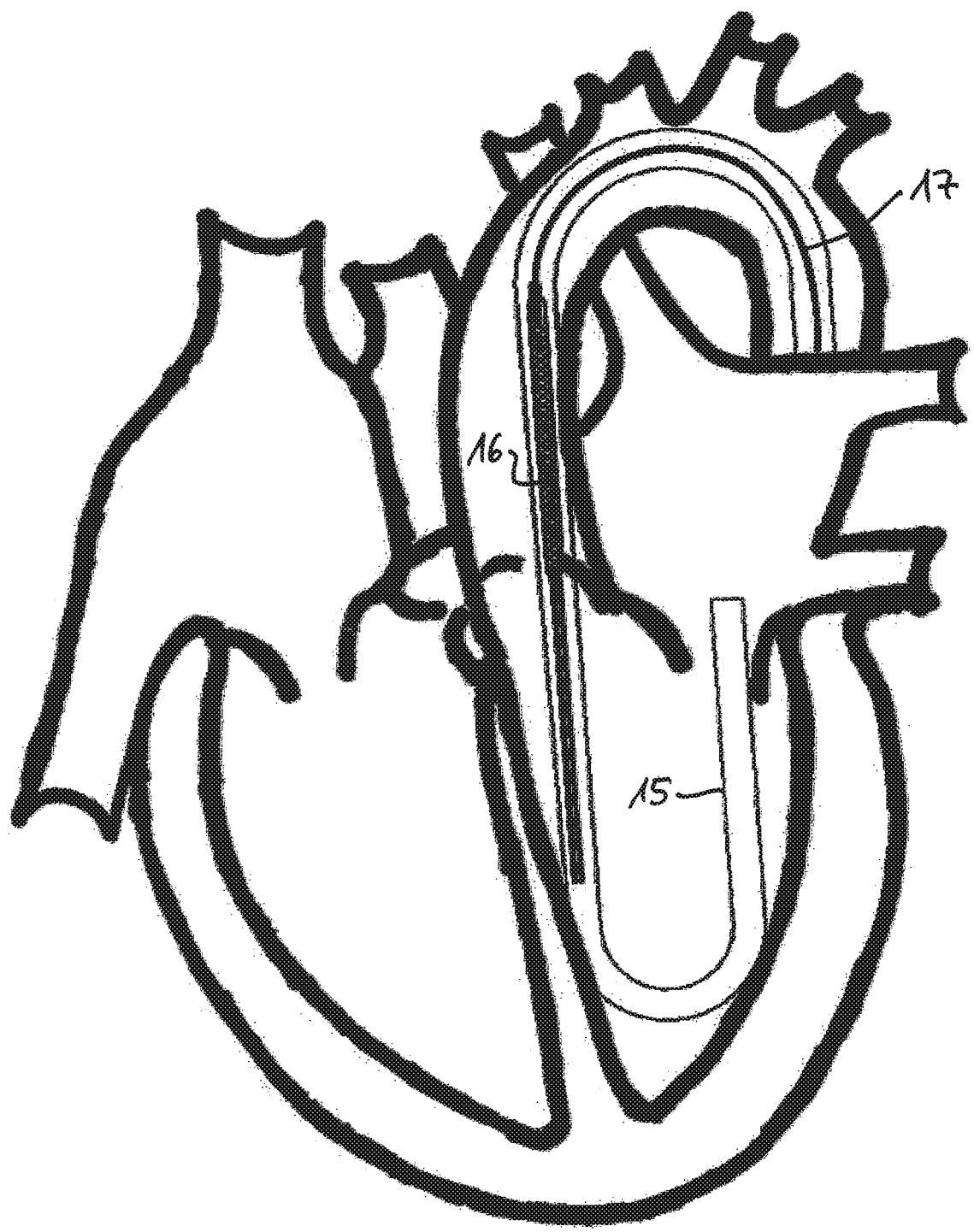
Figure 8B:
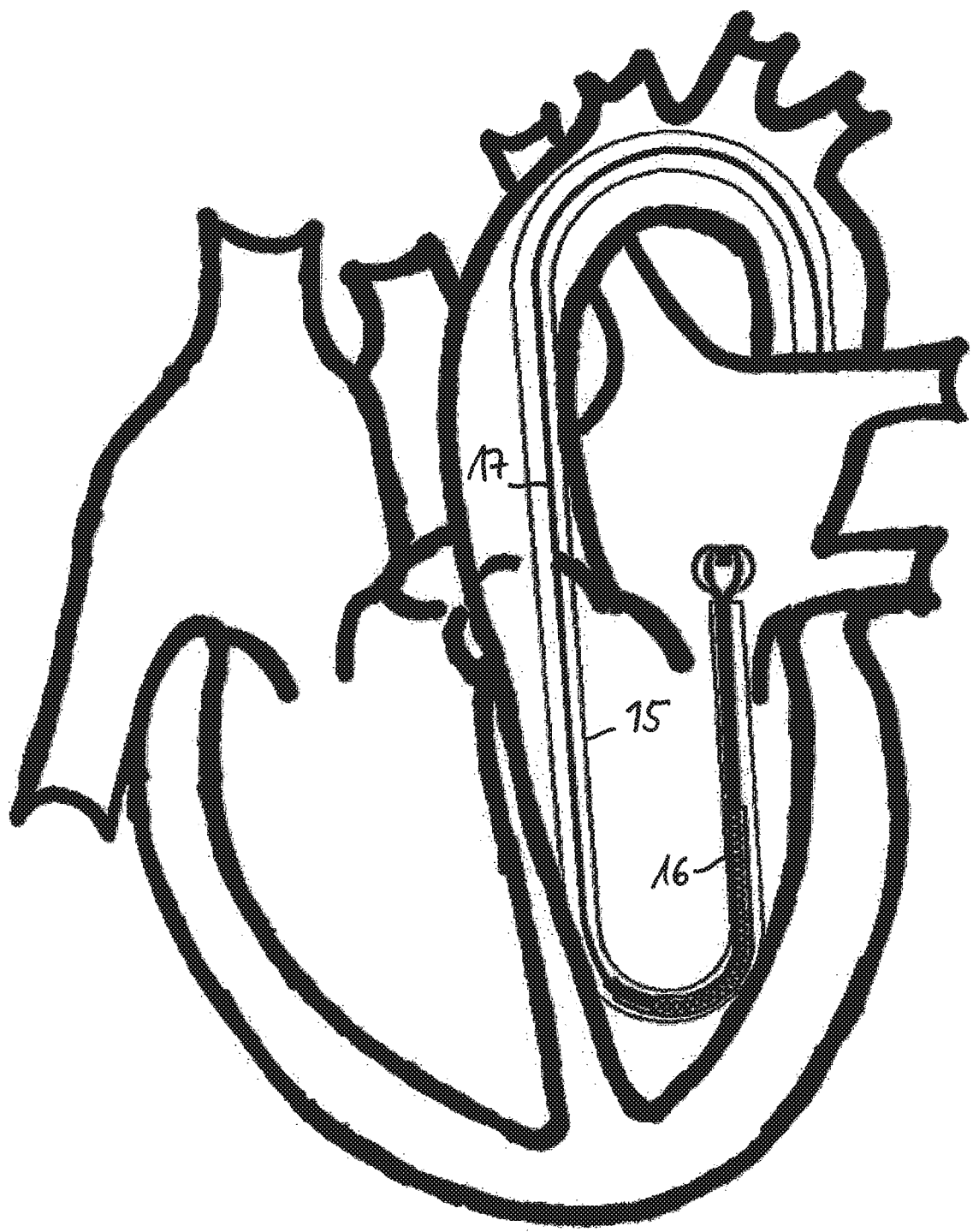

FIG. 8 show the method of implantation and treatment of a diseased heart in more detail. According to FIG. 8A a catheter 15 is forwarded into the heart. The open end of the catheter 15 is passed through the valve annulus and positioned in the atrium of the heart. A collapsed implant 16 is introduced in the catheter 15 and pushed by means of a pushing device 17 until it reaches the atrium. As can be seen in FIG. 8B the implant 16 is released into the atrium and the distal part of the cage starts to expand due to blood contact and the heating to body temperature.

Figure 8C:
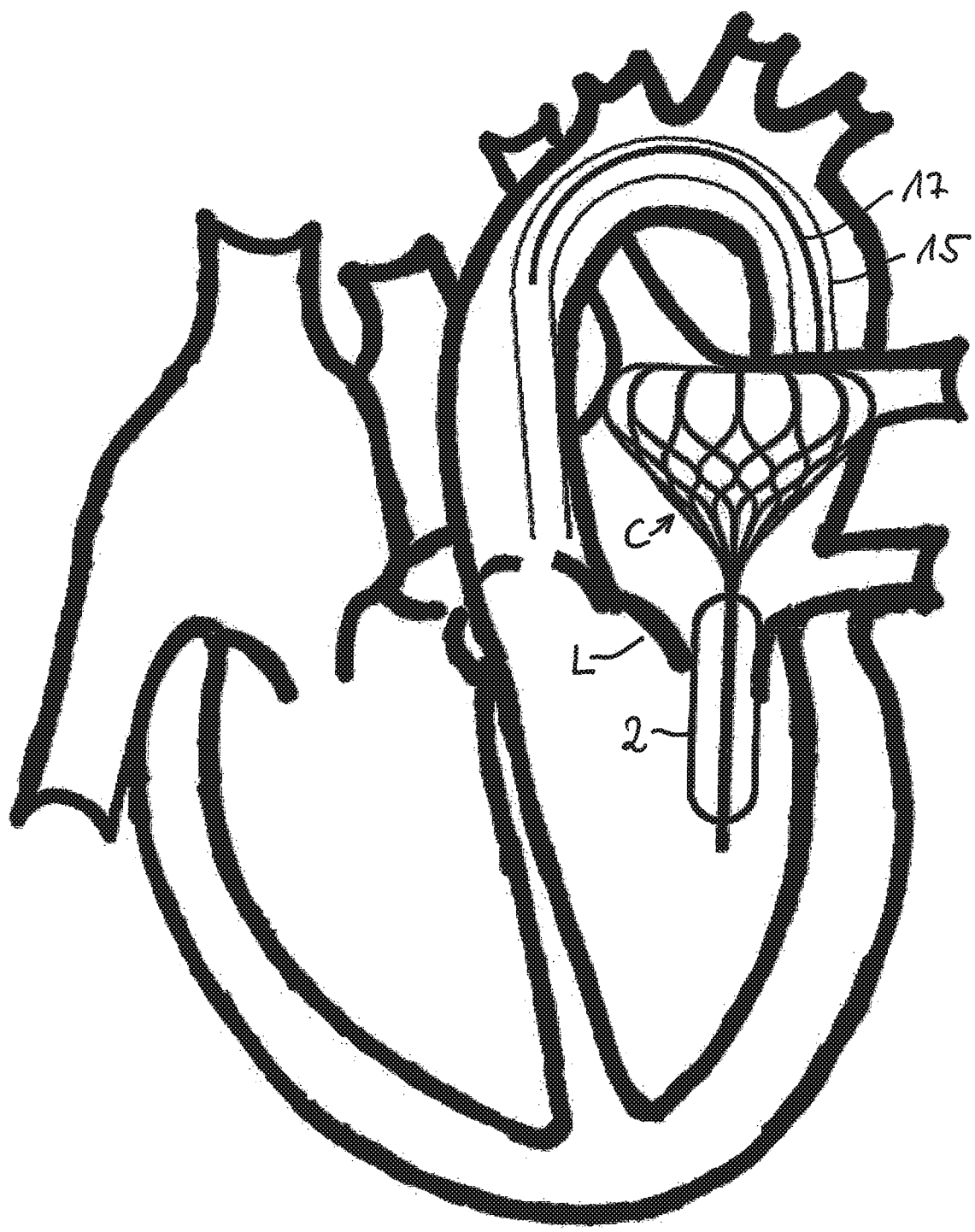

FIG. 8C shows the implant released from the catheter 15 having a totally expanded cage C and membrane 2. The implant is positioned such that the exterior surface of the cage at least in parts contact the inner wall of the atrium and fixes the implant in its desired position. In this position the tubular attachment element 1 and the attached inflated membrane 2 pass through the valve annulus. Accordingly a gap between the closing leaflets L will be reduced or totally prevented, preferably if the leaflets L get into contact with the membrane 2.

The catheter 15 and the pushing device 17 will be retracted and the patient is successfully treated.

In the embodiment of FIG. 8B the end strips 7 are connected to each other, for example as shown in FIG. 1, 3B, 4, 6B or 6C.

Figure 9:
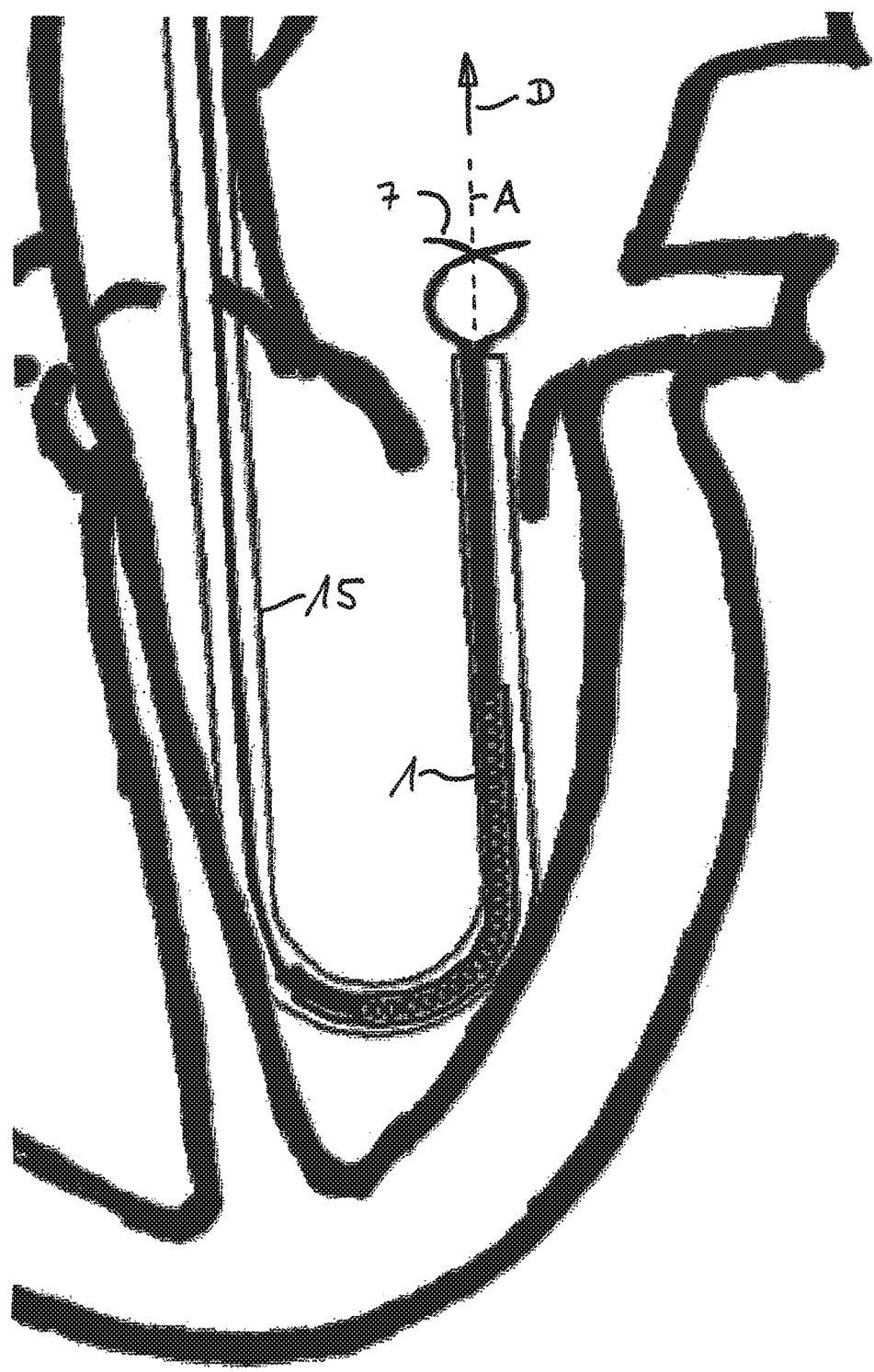

FIG. 9 shows an embodiment of the implant in which the end strips 7 are free, meaning that they are not connected. If the implant it entirely positioned in the catheter these free ends are oriented in parallel to the central axis A of the tubular attachment element 1 as it is also shown in FIG. 8A. If the implant is at least partly released from the catheter as shown in this FIG. 9 the at first released free ends 7 are each bent beyond the central axis A of the tubular attachment element 1, what is shown here for clarity reasons just for two end strips 7. This bending occurs due to the shape-memory effect of the free end that are heated by blood contact. Regarded in a side view each one of the free strips 7 crosses the axis A. The remaining part of the cage is still collapsed and still positioned in the catheter. Accordingly in the direction D of releasing movement there is no risk of puncturing the myocardium with the tips of the free end strips 7 since the tips do not face the myocardium in this direction of movement. Consequently the exact position of the open end of the catheter, particularly its distance to the myocardium is not critical.

When moving forwards and furthermore releasing to implant out of the catheter 15 the cage will furthermore expand and the free ends 7 will be bent even further towards the inner volume of the expanded cage C as shown in the series of FIG. 5.

The invention claimed is:
1. Heart implant comprising
   a. a tubular attachment element (1) for attaching an inflatable membrane (2) being coaxially positioned around the tubular attachment element (1),
   b. the tubular attachment element (1) at one of its ends being split into several strips (4),
   c. the strips (4) extending away from the tubular attachment element (1) and forming an expandable cage (C), for fixing the heart implant to the atrium of the heart by surface contact between an exterior surface of the expandable cage (C) and an interior atrium surface,
   d. each one of the strips (4) being split into two branches (4a, 4b, 4a', 4b', . . . )
   e. each respective branch (4a) being merged into a new strip (5) together with another respective branch (4b') of a neighboring strip (4)
   wherein
   f. such splitting and merging is performed one after the other at least three times
   g. the number of strips (7) being formed of last merged branches (6a, 6b, . . . ) at the end of extension corresponding to the number of strips (4) at the one end of the tubular attachment element (1) wherein the strips (7) at the end of extension form free ends (7) pointing to each other and/or to the central axis (A) of the tubular attachment element (1) and further wherein each of the free ends (7) comprises a pinhole (10).

2. Heart implant according to claim 1, wherein the respective free ends (7) are connected to each other with a suture filament.

3. Heart implant according to claim 2, wherein the respective free ends are connected to a textile connection element (11), by welding/fusing or with a suture filament the connection element (11) surrounding the free ends (7) of the strips at least in the collapsed state of the cage (C).

4. Heart implant according to claim 3, wherein the connection element (11) forms an annular element.

5. Heart implant according to claim 2, wherein each one of the free ends (7) is covered by a respective sleeve (12).

6. Heart implant according to claim 5, wherein the free ends (7) are retractable from the sleeves (12) upon pulling the free ends (7) out of the sleeves (12) with a pulling force.

7. Heart implant according to claim 6, wherein the free ends (7) are retractable only if the pulling force exceeds a set threshold force.

8. Heart implant according to claim 7, wherein the threshold force is defined by the force necessary to overcome a form-closed or force-closed link between a respective end (7) and a link formed by a projection (12a) on an inner surface of the sleeve (12) being positioned in a depression (7a) on an outer surface of the end (7).

9. Heart implant according to claim 5, wherein the respective sleeves (12) are connected to each other.

10. Heart implant according to claim 9, wherein the respective sleeves (12) are connected to an annular element (13), the annular element (13) surrounding the central axis (A) of the tubular attachment element (1).

11. Heart implant according to claim 2, wherein in the expanded state of the cage (C) the free ends (7) of the strips are positioned between a proximal part (PP) of the cage (C) and a distal part (DP) of the cage (C).

12. Heart implant according to claim 2, wherein in the expanded state of the cage (C) the respective free ends (7) are bent towards or into the inner volume of the cage (C).

13. Heart implant according to claim 12, wherein in the expanded state of the cage (C) the respective free ends (7) are parallel to the central axis (A) of the tubular attachment element (1).

14. Method of treating heart valve insufficiency of a diseased heart valve having a remaining gap between closed valve leaflets, comprising:
   a. delivering a heart implant according to claim 1 via a catheter to the heart of a mammalian patient, preferably a human,
   b. releasing the implant out of the catheter into the heart,
   c. positioning the implant such that the cage is arranged in the atrium of the heart and the tubular attachment element having a membrane attached to it passes through the valve annulus,
   d. anchoring the implant to the atrium by expanding the cage and thus forcing the exterior surface of the cage to contact the inner heart wall of the atrium,
   e. reducing blood regurgitation by expanding the membrane and thus preventing or reducing the remaining gap between the closed valve leaflets,
   f. removing the catheter.

* * * * *